(12) United States Patent
Nguyen et al.

(10) Patent No.: US 12,383,245 B2
(45) Date of Patent: Aug. 12, 2025

(54) ENDOSCOPIC STRIP DELIVERY DEVICE

(71) Applicant: BOSTON SCIENTIFIC SCIMED, INC., Maple Grove, MN (US)

(72) Inventors: Phuc Huu Nguyen, Houston, TX (US);
Samuel Goshen, Brookline, MA (US);
Jeffrey V. Bean, Fitchburg, MA (US);
Megan Dunkin, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 147 days.

(21) Appl. No.: 18/522,914

(22) Filed: Nov. 29, 2023

(65) Prior Publication Data
US 2024/0197305 A1   Jun. 20, 2024

Related U.S. Application Data

(60) Provisional application No. 63/387,736, filed on Dec. 16, 2022.

(51) Int. Cl.
*A61B 17/00*   (2006.01)

(52) U.S. Cl.
CPC .. *A61B 17/00491* (2013.01); *A61B 17/00234* (2013.01); *A61B 2017/0034* (2013.01); *A61B 2017/00951* (2013.01)

(58) Field of Classification Search
CPC ........ A61B 17/00491; A61B 17/00234; A61B 17/295; A61B 17/320016; A61B 17/3201; A61B 2017/0034; A61B 2017/00951; A61B 2017/12004; A61B 17/1227; A61B 17/1285; A61B 17/12; A61B 17/083
See application file for complete search history.

(56) References Cited

U.S. PATENT DOCUMENTS

| 9,161,756 | B2 | 10/2015 | Sargeant et al. |
| 2010/0121367 | A1 | 5/2010 | Lin et al. |
| 2020/0237357 | A1* | 7/2020 | Cao ................... A61B 17/00491 |

* cited by examiner

*Primary Examiner* — Anh T Dang
(74) *Attorney, Agent, or Firm* — Fay Kaplun & Marcin, LLP (57) ABSTRACT

A device includes a body and a clipping mechanism including first and second clipping members. At least the first member is rotatably coupled to a distal end of the body so that the mechanism transitions between Closed State, in which distal ends of the members are in abutting contact, and Open State, in which the first member is rotated away from the second member to allow an adhesive material to be extended distally past the distal ends. A working channel of the device is formed in the body and components of the mechanism. The channel extends longitudinally through the device so that the material passes into a proximal end of the channel, through the channel, and distally past the distal ends when the mechanism is in Open State, whereupon the mechanism transitions into Closed State and a portion of the material severed and applied to target.

20 Claims, 5 Drawing Sheets

ENDOSCOPIC STRIP DELIVERY DEVICE

PRIORITY CLAIM

The present disclosure claims priority to U.S. Provisional Patent Application Ser. No. 63/387,736 filed Dec. 16, 2022; the disclosure of which is incorporated herewith by reference.

FIELD

The present disclosure relates to an adhesive material delivery device for use with an endoscope.

BACKGROUND

A minimally invasive medical device, such as an endoscope, may include a flexible elongate shaft comprising one or more channels through which a medical instrument can be run and/or controlled. Generally, an operating physician guides the endoscope to a target site within a living body (e.g., by passing the endoscope through a body lumen accessed, for example, via a body orifice) using an endoscopic camera or other guidance means so that a medical instrument may be used at the target site.

Internal bleeding in the gastrointestinal (GI) tract and stomach can be caused by ulcers, cancers, polyps, or other biological growths or diseases and can be fatal or cause irreversible organ damage. In nearly all cases, the patient requires an endoscopic procedure to stop the bleeding at these sites. Many current endoscopic procedures for stopping internal bleeding in the GI tract rely on surgery and other invasive maneuvers such as electro-cautery, clamps, lasers, injections of sclerosing agents, etc.

To avoid such invasive maneuvers, it is desirable to use only the endoscopic system to stop internal bleeding in the GI tract. In some scenarios, a mucoadhesive material, e.g., chitosan, can be deployed in thin strips or wires at the bleed site to stanch the blood flow. However, delivering thin planar strips of mucoadhesive material down the length of an endoscope to a target site can prove difficult for various reasons. In one example, the material may be a thin rectangular strip with sharp corners that is prone to buckling or catching within internal geometries of the endoscope shaft. In another example, it may be difficult to accurately place the material on the bleed site.

SUMMARY

The present disclosure relates to a device for applying an adhesive material to a target site in an endoscopic procedure. The device includes a body sized and shaped to be passed through an endoscope working channel of an endoscope; and a clipping mechanism comprising first and second clipping members. At least the first clipping member is rotatably coupled to a distal end of the body so that the clipping mechanism can be transitioned between a closed state, in which distal ends of the clipping members are in abutting contact, and an open state, in which the first clipping member is rotated away from the second clipping member to allow the adhesive material to be extended distally past the distal ends of the clipping members. A device working channel of the device is formed in the body and components of the clipping mechanism, the device working channel extending longitudinally through an entirety of the device so that the adhesive material can be passed into a proximal end of the device working channel, through the device working channel, and distally past the distal ends of the clipping members when the clipping mechanism is in the open state, whereupon the clipping mechanism can be transitioned into the closed state and a portion of the adhesive material can be severed and applied to the target site.

In an embodiment, the adhesive material is formed into a strip and the device working channel comprises an oval or rectangular cross section for guiding the strip through the device.

In an embodiment, the body comprises a proximal portion including a channel and the clipping mechanism includes a plunger, the channel being sized and shaped to receive the plunger, wherein the device working channel extends through the plunger.

In an embodiment, the clipping mechanism includes a joining member coupled to or formed with the plunger, wherein a proximal end of at least a first lever member is rotatably coupled to the joining member and a proximal end of the first clipping member is rotatably coupled to a distal end of the first lever member, wherein the device working channel extends through the joining member.

In an embodiment, in the closed state, the plunger is in a proximal position in the channel, the proximal end of the first lever member is in a proximal position, and the first clipping member extends distally.

In an embodiment, in the open state, the plunger is in a distal position in the channel, the proximal end of the first lever member is in a distal position, and the first lever member and the first clipping member are rotated so that the distal end of the first clipping member is rotated away from the second clipping member.

In an embodiment, the distal end of at least the first clipping member comprises a sharp edge for severing the adhesive material.

In an embodiment, the device working channel comprises a slot formed in at least the first clipping member.

In an embodiment, the second clipping member is rotatably coupled to the distal end of the body and, when the device is transitioned into the open state, the second clipping member is rotated away from the first clipping member.

In an embodiment, the first clipping member is biased to rotate in a first direction and the second clipping member is biased to rotate in a second direction opposite the first direction when the clipping mechanism is actuated via longitudinal translation of a plunger of the clipping mechanism.

In an embodiment, the first clipping member is rotatably coupled to distal end of the body via a pin extending through pin holes in the first clipping member and the distal end of the body.

In an embodiment, the adhesive material is formed as a wire and the device working channel comprises a circular cross-section for guiding the strip through the device.

In an embodiment, the second clipping member is fixed or formed integrally with the distal end of the body and the first clipping member and only the first clipping member is rotatable to open or close the clipping mechanism.

In an embodiment, the clipping mechanism is actuated by a pull wire coupled to a proximal end of the clipping mechanism.

In an embodiment, the adhesive material is chitosan.

In addition, the present disclosure relates to a method for applying an adhesive material to a target site in an endoscopic procedure. The method includes passing a material delivery device through an endoscope working channel of an endoscope, the device comprising a body sized and shaped to be passed through the endoscope working channel and a clipping mechanism comprising first and second clipping members, at least the first clipping member being rotatably coupled to a distal end of the body so that the clipping mechanism can be transitioned between a closed state, in which distal ends of the clipping members are in abutting contact, and an open state, in which the first clipping member is rotated away from the second clipping member to allow the adhesive material to be extended distally past the distal ends of the clipping members, wherein a device working channel of the device is formed in the body and components of the clipping mechanism, the device working channel extending longitudinally through an entirety of the device; passing the adhesive material through the endoscope working channel into a proximal end of the device working channel, through the device working channel, and distally past the distal ends of the clipping members when the clipping mechanism is in the open state; and transitioning the clipping mechanism into the closed state to sever a portion of the adhesive material and apply the portion of the adhesive material to the target site.

In an embodiment, the adhesive material is formed into a strip and the device working channel comprises an oval or rectangular cross section for guiding the strip through the device.

In an embodiment, the adhesive material is formed into a wire and the device working channel comprises a circular cross section for guiding the strip through the device.

In an embodiment, the clipping mechanism is actuated by a pull wire coupled to a proximal end of the clipping mechanism.

In an embodiment, the method further includes after applying the portion of the adhesive material to the target site, transitioning the clipping mechanism into the open state; passing a remaining portion of the adhesive material distally past the distal ends of the clipping members; and transitioning the clipping mechanism into the closed state to sever a further portion of the adhesive material and apply the further portion of the adhesive material to the target site.

BRIEF DESCRIPTION

DETAILED DESCRIPTION

The present disclosure may be further understood with reference to the following description and the appended drawings, wherein like elements are referred to with the same reference numerals. The present disclosure relates to a material delivery device for deploying and manipulating the application of an adhesive material to a target site in an endoscopic procedure. The material delivery device can be passed through the working channel of an endoscope, e.g., a duodenoscope, and extend distally out the distal end of the endoscope to access a target site within a living body, e.g., a bleed site in the gastrointestinal (GI) tract. The adhesive material can comprise, for example, a strip or wire that is passed through the device and distally out of the distal end of the device for placement on or around the bleed site. When the adhesive material is extended to a desired length, a clipping mechanism of the device can be actuated to sever the material and apply the material to the target site.

In one aspect of these exemplary embodiments, the device comprises a working channel extending therethrough that is sized and shaped to guide the adhesive material through the device to the target site while avoiding buckling, twisting, or other undesirable effects that could complicate the application of the strip at the target site. In one embodiment, the device working channel has an elliptical, oval or rectangular geometry for guiding a thin rectangular strip of adhesive material. In another embodiment, the working channel has a circular geometry for guiding a wire of the adhesive material. The strip/wire can be passed through the endoscope and through the working channel of the device so that a user, e.g., an operating physician, can project the material distally out of the device and/or withdraw the strip proximally into the device during the endoscopic procedure. In one embodiment, the adhesive material is fixed or coupled to a push/pull wire. In another embodiment, the adhesive material is pre-loaded within the device. The adhesive material may be, e.g., a thin rectangular strip of a mucoadhesive material such as, e.g., chitosan. It should be understood that the device working channel extends through multiple parts of the device, including the body and aspects of the shearing or clipping mechanism, to be described in greater detail below.

In another aspect of these exemplary embodiments, the device comprises a shearing or clipping mechanism for severing the adhesive material to a custom length at the discretion of the user. In one embodiment, the clipping mechanism comprises two clipping members, e.g., shears, having distal edges sufficiently sharp to sever the adhesive material. In another embodiment, the clipping mechanism comprises a first clipping member having a sharp edge and a second clipping member providing a surface (e.g., an anvil) against which the first clipping member can be drawn to cut the adhesive material, e.g., similar to a guillotine.

The clipping members of the clipping mechanism, e.g., the shears, can be transitioned between a closed state, in which the first and second clipping members extend substantially longitudinally and the distal edge(s) of the clipping members are in abutting contact with one another, and an open state, in which the distal edge(s) of the first clipping member and/or the second clipping member are rotated apart from one another and are separated by a distance sufficient to allow the adhesive material to pass therebetween. In one exemplary scenario, the device is passed through the endoscope and brought adjacent to the target site with the clipping members in the closed state, whereupon the clipping members are separated (opened), the adhesive material is passed through the device and extended between the clipping members to a desired length and applied to the target site. The clipping members are then closed to sever the portion of the adhesive material that is applied to the target site from any portion(s) of strip/wire remaining in the device.

This process can be repeated multiple times. For example, the strip/wire can be extended to the target site, severed, extended again and severed again, so long as additional material remains in the device. The strip/wire can comprise any length and can be passed through the device in a continuous manner. If a particular strip has been exhausted of material (e.g., most or all of the adhesive material has been applied to one or more target sites) yet the user desires to apply further adhesive material to a further target site (or to apply more to a previously treated target site), a further strip of adhesive material may be passed through the device (e.g., where the device extends through an endoscope) to complete the procedure.

The clipping mechanism further comprises a lever system for actuating the opening and closing of the clipping members. In one embodiment, the two clipping members are rotatable in opposing directions about respective pins at the distal tip of the device via respective lever arrangements operating in coordination with one another. The two clipping members can be rotated apart to transition the clipping mechanism from the closed to the open state, and the two clipping members can be rotated toward each other to transition the clipping mechanism from the open state into the closed state. In another embodiment, only a first clipping member is rotatable and the second clipping member remains in a fixed position relative to the first clipping member. The lever arrangements can be actuated by a longitudinally translatable member, e.g., a plunger, in the body/shaft of the device that can be controlled by the user via a push/pull wire actuated via an actuator that remains outside the body accessible to the user. The assembly and operation of the lever system will be described in greater detail below.

In another aspect of these exemplary embodiments, the device may include an articulation mechanism for providing greater control to the user during operation. For example, a sleeve comprising one or more pull wires, e.g., a Bowden cable, may be fixed to a proximal end of the body/shaft.

Figure 7:
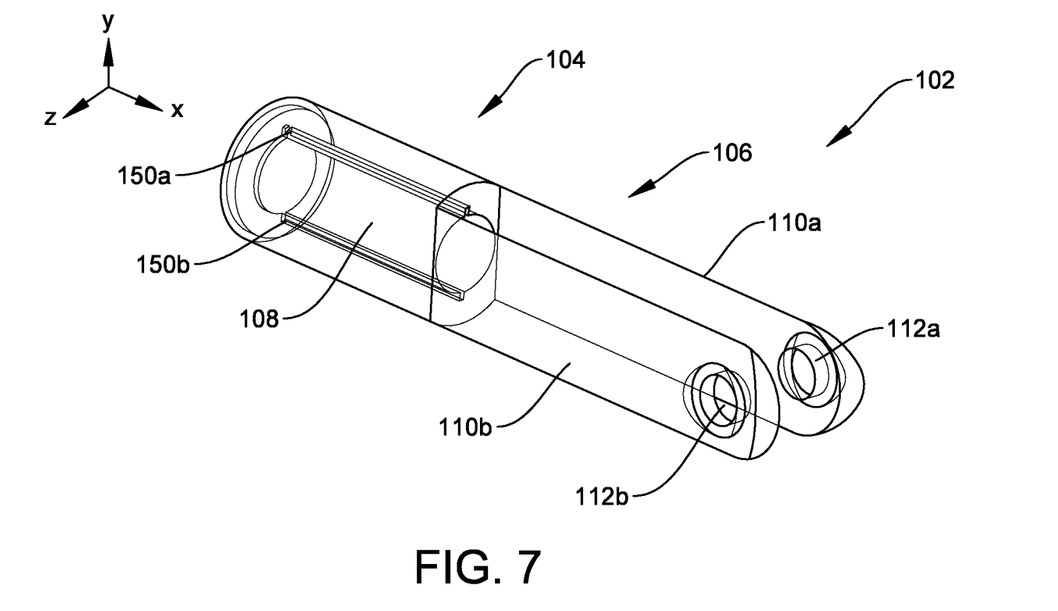
FIG. 7 shows a perspective view of a body of the material delivery device of FIGS. 1-6.

FIGS. 1-6 show an exemplary embodiment of a material delivery/application device 100 for deploying and manipulating the application of an adhesive material in an endoscopic procedure according to various exemplary embodiments. FIG. 7 shows a body 102 of the device 100 of FIGS. 1-6 and FIG. 8 shows a clipping mechanism 120 of the device 100 of FIGS. 1-6. As shown in FIGS. 1-8, the device 100 is described with respect to a coordinate system wherein the X axis extends along the longitudinal axis of the device 100, the Y axis extends in a first direction transverse to the X axis, and the Z axis extends in a second transverse direction orthogonal to the X and Y axes. The device 100 is sized and shaped to be passed through the working channel of an endoscope, e.g., a duodenoscope, and extend distally beyond the distal end of the endoscope to access a target site within a living body.

Figure 8:
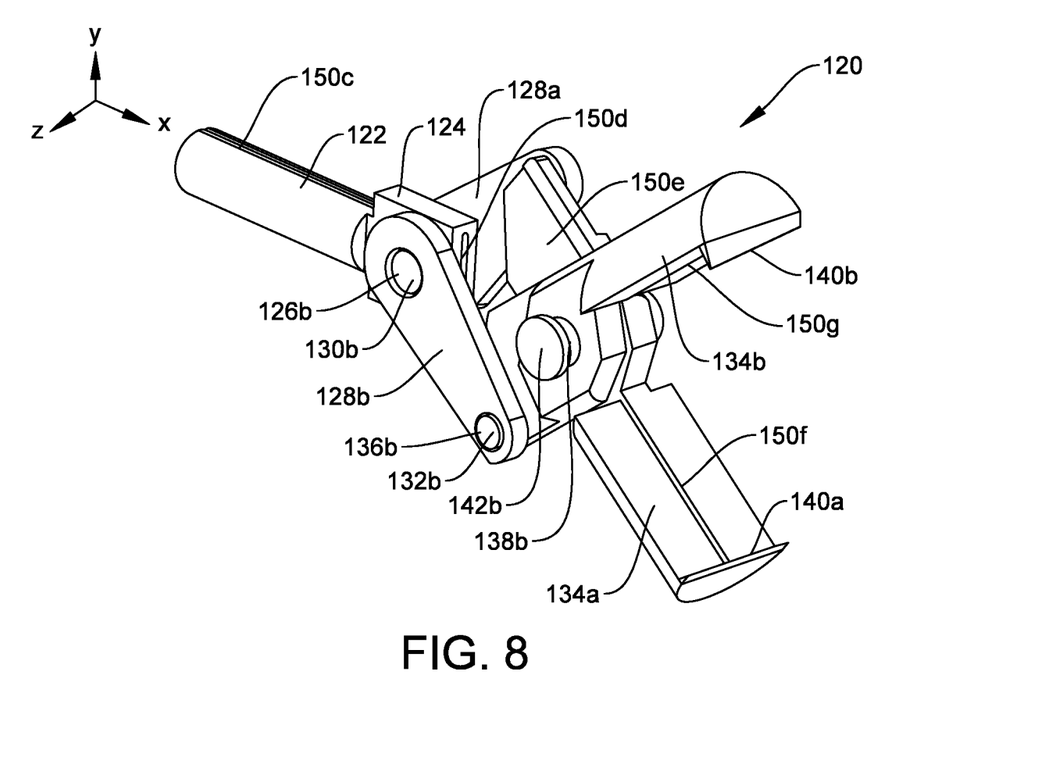
FIG. 8 shows a perspective view of the cutting mechanism of the material delivery device of FIGS. 1-6 with the cutting mechanism in the open state.

The device 100 comprises the body 102 including a proximal portion 104 and a distal portion 106 formed as a single unitary piece, as shown in FIG. 7, and a clipping mechanism 120 including two clipping members 134 (e.g., a first clipping member 134a and a second clipping member 134b) actuated by a lever system, as shown in FIG. 8. The body 102 is assembled with the clipping mechanism 120, as shown in FIGS. 1-6. The device 100 has a hollow geometry, e.g., a working channel 150, that extends longitudinally through the entirety of the device 100, as shown in the cross-sectional view of FIG. 5. The working channel 150 extends through multiple parts of the device 100 including the body 102 and components of the clipping mechanism 120 to allow an adhesive material to be passed through the device 100 from a proximal end (e.g., which, during use, remains outside the body accessible to the user) to extend distally from the distal end of the distal portion 106 and distally past clipping ends 140 of the clipping members 134 so that the clipping ends 140 may be operated to sever an extended portion of the adhesive material from a remaining portion proximal of the clipping ends 140 as will be described in greater detail below.

The proximal portion 104 of this embodiment has a cylindrical exterior and a channel 108 extending longitudinally therethrough although other cross-sectional shapes may be employed as desired. The channel 108 is sized to receive a cylindrical plunger 122 of the clipping mechanism 120 as will be described in greater detail below. The distal portion 106 comprises two longitudinal members 110, e.g., a first longitudinal member 110a and a second longitudinal member 110b, extending distally along opposing sides of the proximal portion 104, each of the longitudinal members 110 includes a pin hole 112, e.g., a first pin hole 112a and a second pin hole 112b, at the distal end for coupling to a respective clipping member 134 of the clipping mechanism 120 to the distal end of the body 102, as shown in FIG. 7 and as described in greater detail below.

Figure 3:
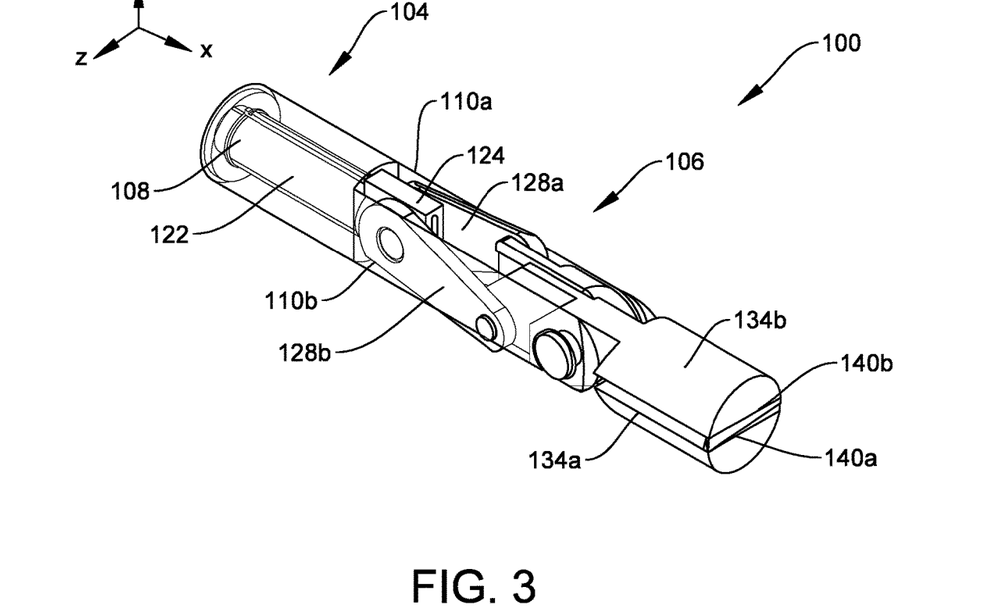
FIG. 3 shows a perspective view of the material delivery device of FIG. 1 with a cutting mechanism in a closed state.
Figure 4:
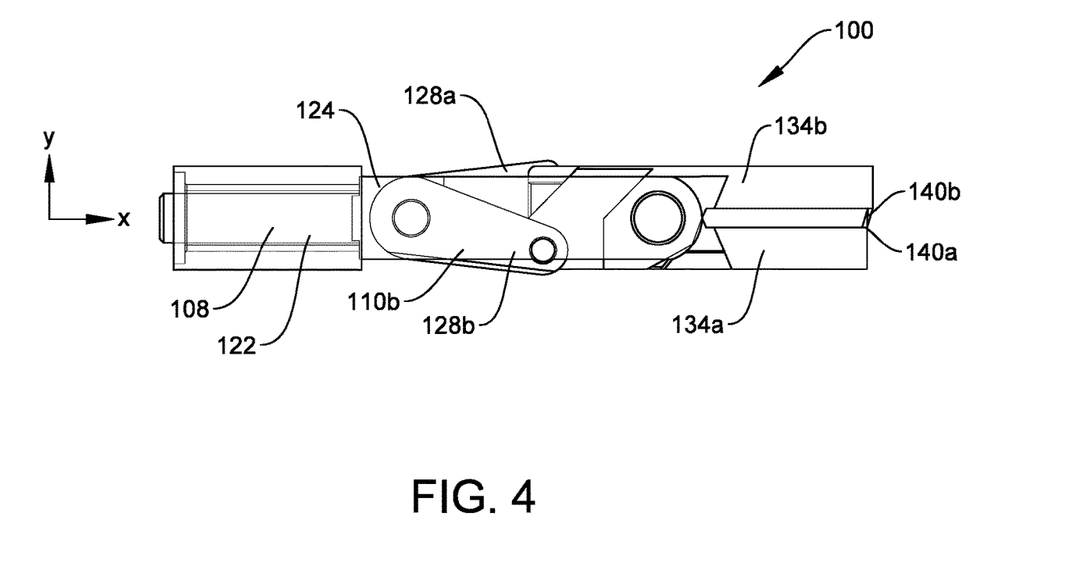
FIG. 4 shows a side view of the material delivery device of FIG. 1 with the cutting mechanism in the closed state.
Figure 5:
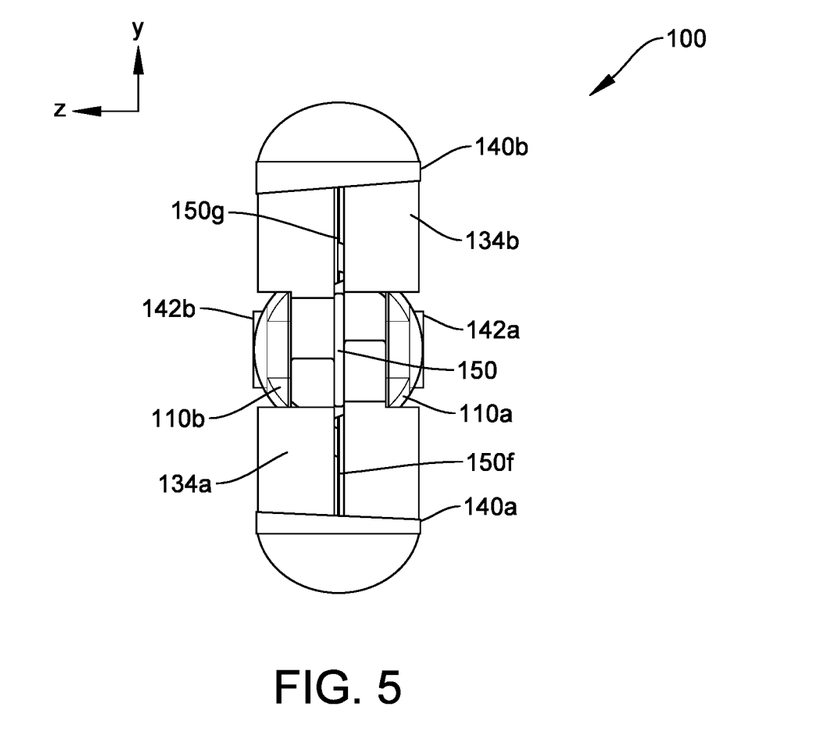
FIG. 5 shows a section view of the material delivery device of FIG. 1 with the cutting mechanism in the open state.
Figure 6:
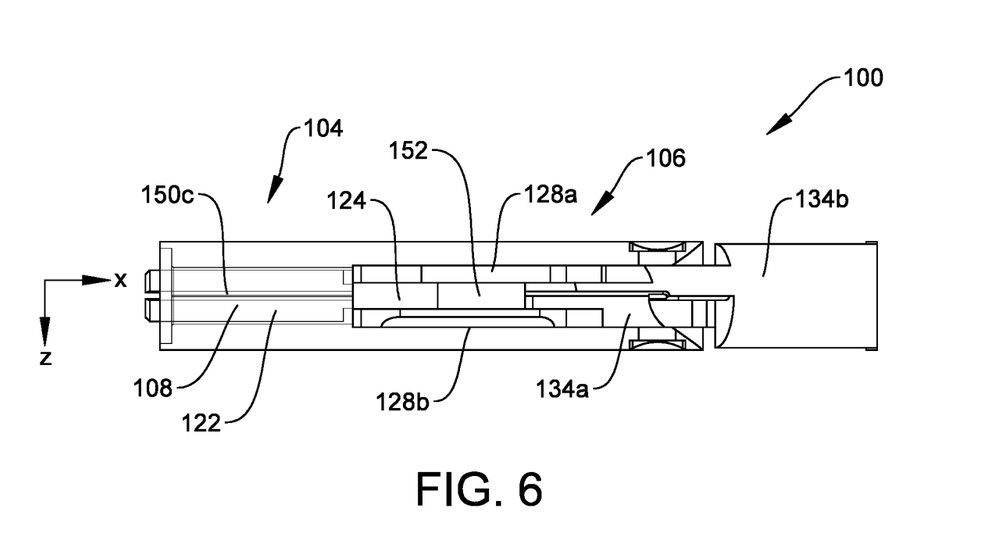
FIG. 6 shows a top view of the material delivery device of FIG. 1 with the cutting mechanism in the closed state.

In the exemplary embodiment of the present disclosure shown in FIGS. 1-8, the device 100 is designed for the application of a thin strip of the adhesive material, specifically, sections of a long strip that are cut to custom lengths. The working channel 150, as shown in the cross-sectional view of FIG. 5, is oval in shape to guide the strip through and out the distal end of the device 100. The working channel 150 may also be rectangular. The working channel 150 is sized and shaped to guide the strip through the device 100 to the target site while avoiding buckling, twisting, etc., e.g., has a width (extending along the y-axis) slightly larger than the width of the adhesive strip and a depth (extending along the z-axis) slightly larger than the depth of the adhesive strip—i.e., a clearance designed to facilitate the movement of the adhesive through the working channel 150 while closely matched to the size and shape of the adhesive strip so that it moves longitudinally through the working channel 150 without room for buckling or twisting. In other embodiments, the device 100 is designed for the application of wires of adhesive material and the working channel 150 can comprise a cross-section to substantially matching the size and shape of the outer profile of the wires (e.g., circular).

In this example, the working channel 150 extending through the entirety of the device 100 is slightly wider than the channel 108 that extends through the proximal portion 104 of the body 102 and which is configured to receive the plunger 122 of the cutting mechanism 120. The channel 108 has radial extensions 150a, 150b forming radially outer ends of the working channel 150 that are sized and shaped to hold radially outer portions the adhesive strip (that extend, in this embodiment, radially beyond an outer diameter of the plunger 122) while the center of the adhesive strip is received within the channel 108 to align the adhesive strip as it passes through the proximal portion of the body 102. The proximal ends of the radial extensions 150a, 150b of the channel 108 are curved (chamfered) to facilitate guiding of the strip into the working channel 150 and the channel 108. As would be understood by those skilled in the art, the proximal ends of the channel 108 may be similarly chamfered to facilitate the introduction of the adhesive strip therein.

In some embodiments, as described above, the adhesive strip is passed through the endoscope separately from the device 100, e.g., after the device 100 has been passed through the endoscope to a position adjacent to the target site. In other embodiments, an adhesive strip may be preloaded in the device 100 before the device 100 is inserted into the endoscope. As would be understood by those skilled in the art, the adhesive strip may be formed of any desired length. For example, the adhesive strip may be relatively short (i.e., comprising an amount of material sufficient to apply only one or a few portions of the adhesive strip (severed from the remainder of the strip) to the target site before the material is exhausted. In another example, the adhesive strip may be relatively long and comprise material sufficient to apply many portions of the strip to the target site. In some embodiments, the strip can be coupled on a proximal end to a pull wire or a plunger mechanism operable by the user proximal to the proximal end of the endoscope.

The strip is guided through the working channel 150 of the device 100 and severed by the clipping members 134, e.g., shears, of the clipping mechanism 120 when the material is extended past the clipping ends 140 by a desired length. After the desired length of the adhesive strip has been extended past the distal ends of the clipping members 134, the user operates an actuator (not shown) to move the clipping members 134 from the open state to the closed state via a lever system including the plunger 122, a joining member 124 and a respective lever member 128 coupled to each of the clipping members 134 as will be described in greater detail below. In the closed state, the first and second clipping members 134a, 134b extend substantially longitudinally from the distal portion 106 with the clipping ends 140 in abutting contact with each other.

In this embodiment, in the closed configuration, the first and second clipping members 134a, 134b combine to form a unit having cross-section similar that of the outer diameter of the proximal portion 104 of the body 102, as shown in FIGS. 3-4. This facilitates passage of the device 100 through the working channel 150 of the endoscope while the clipping members 134 are maintained in the closed state so that the clipping members 134 may be brought adjacent to a target site in the body. In addition, this facilitates the passage of the adhesive strip to the distal ends of the clipping members 134 as slots 150f, 150g in the first and second clipping members 134a and 134b, respectively, guide the adhesive strip as it is advanced distally until it contacts inner (proximal) surfaces of the clipping ends 140.

Figure 1:
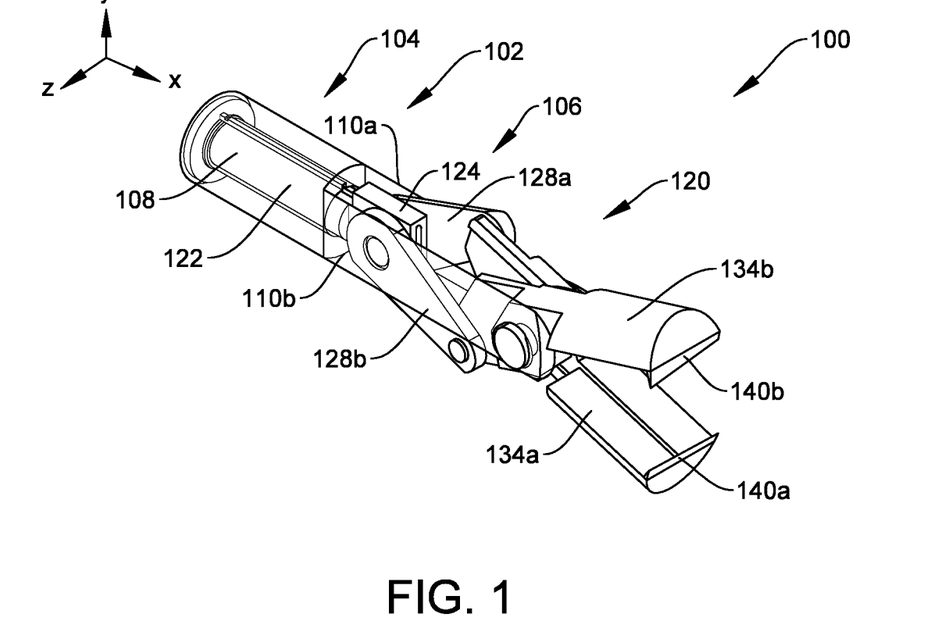
FIG. 1 shows a perspective view of a material delivery device for deploying and manipulating the application of an adhesive material in an endoscopic procedure according to various exemplary embodiments, wherein a cutting mechanism of the device is in an open state.
Figure 2:
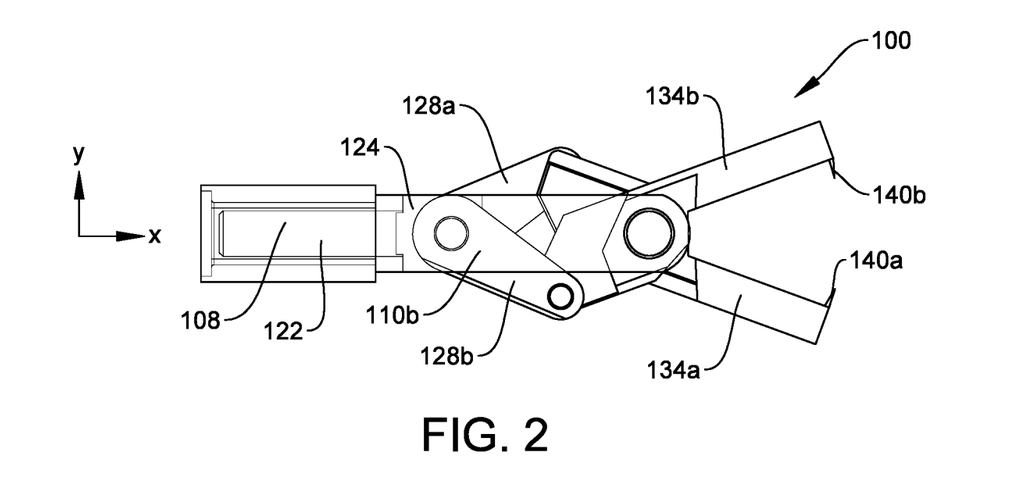
FIG. 2 shows a side view of the material delivery device of FIG. 1 with the cutting mechanism in the open state.

The first and second clipping members 134a, 134b can then be rotated apart from one another into the open configuration so that the adhesive strip can be advanced further distally to expose a desired length of the adhesive strip, as shown in FIGS. 1-2. When a desired length of the adhesive material is positioned to the satisfaction of the operating physician, the first and second clipping members 134a, 134b are rotated together into the closed position to sever the material to the selected custom length.

As indicated above, the clipping members 134 can be transitioned between the open state and the closed state via a lever system of the clipping mechanism 120 that is actuated by a push/pull wire connected to an actuator that remains accessible to the user when the distal portion of the device 100 is inserted into the body. In this example, the clipping mechanism 120 comprises a plunger 122, a joining member 124, two lever members 128 and two clipping members 134, e.g., a first lever member 128a coupled to the first clipping member 134a and a second lever member 128b coupled to the second clipping member 134b, as shown in FIG. 8.

The plunger 122 is fixedly coupled to or integrally formed with the joining member 124. The joining member 124 comprises two joining pins 126 extending outward (relative to the longitudinal axis of the device 100) from opposing sides of the joining member 124, e.g., in the same direction as the z-axis. The joining pins 126 are sized and shaped to be received in (e.g., rotatably coupled to) corresponding proximal pin holes 130 in the lever members 128. That is, the joining member 124 is rotatably coupled to a first lever member 128a via a first joining pin 126a received in a first proximal pin hole 130a of the first lever member 128a and the joining member 124 is rotatably coupled to a second lever member 128b via a second joining pin 126b received in a second proximal pin hole 130b of the second lever member 128b.

Each of the lever members 128 includes two pin holes, e.g., a proximal pin hole 130 and a distal pin hole 132. Each of the clipping members 134 includes a proximal pin 136 extending outward (relative to the longitudinal axis of the device 100), e.g., in the same direction as the z-axis. The proximal pins 136 are sized and shaped to be received in (e.g., rotatably coupled to) corresponding distal pin holes 132 in the lever members 128. That is, the first lever member 128a is rotatably coupled to the first clipping member 134a via a first proximal pin 136a of the first clipping member 134a received in a first distal pin hole 132a of the first lever member 128a and the second lever member 128b is rotatably coupled to the second clipping member 134b via a second proximal pin 136b of the second clipping member 134b received in a second distal pin hole 132b of the second lever member 128b.

Each of the clipping members 134 comprises a pin hole 138 sized and shaped to receive a respective body pin 142 for rotatably coupling the clipping members 134 to the longitudinal members 110 of the distal portion 106 of the body 102. That is, the first clipping member 134a is rotatably coupled to the first longitudinal member 110a via a first body pin 142a and the second clipping member 134b is rotatably coupled to the second longitudinal member 110b via a second body pin 142b.

When the body 102 and the clipping mechanism 120 are assembled, the lever system described above can be actuated to transition the clipping members 134 between the closed state and the open state. The lever system can be actuated via a push/pull wire coupled to the proximal end of the plunger 122. The plunger 122 is slidable longitudinally within the channel 108 of the proximal portion 104 of the body 102 and so that longitudinal movement of the plunger 122 translates the joining member 124 longitudinally. The translation of the joining member 124 causes the lever members 128 and the clipping members 134 to translate and/or rotate in the following manner.

The proximal ends of the lever members 128 are rotatably coupled to the joining member 124. Thus, the proximal ends of the lever members 128 translate along with the joining member in the longitudinal direction, while the lever members 128 are free to rotate about the joining pins 126. The distal ends of the lever members 128 are rotatably coupled to the proximal ends of the clipping members 134, and the clipping members 134 are rotatably coupled to the distal ends of the distal portion 106 of the body 102. Thus, the clipping members 134 are positionally fixed to the body 102 but free to rotate about the body pins 142. The rotation of the clipping members 134 moves the proximal ends of the clipping members 134 longitudinally (in the direction of the x-axis) and transversely (in the direction of the y-axis). Thus, the distal ends of the lever members 128 translate with the proximal ends of the clipping members while rotating about the proximal pins 136 of the clipping members 134.

In one embodiment, the first lever member 128*a* and the first clipping member 134*a* are biased so that, when not acted on by an outside force, the first clipping member 134*a* rotates in a first direction (e.g., the −y direction) while the second lever member 128*b* and the second clipping member 134*b* are biased so that the second clipping member 134*b* rotates in a second direction (e.g., the +y direction) opposite the first direction when the clipping mechanism 120 is transitioned from the closed state to the open state.

As described previously, the working channel 150 extends through the entirety of the device 100. This includes the radial extensions 150*a*, 150*b*, e.g., first and second aspects of the working channel 150, extending radially from the channel 108 of the proximal portion of the body 102, as described above, and a third aspect formed as a slot 150*c* extending through the plunger 122 of the clipping mechanism 120. The slot 150*c* bisects the plunger 122 and, in combination with the radial extensions 150*a*, 150*b*, guides the adhesive strip through the proximal portion 104 of the body 102.

The working channel 150 continues into a slot 150*d*, e.g., a fourth aspect of the working channel, extending through the joining member 124. A gap 152 extends between the joining member 124 and the clipping members 134, as shown in the overhead view of FIG. 6. A fifth aspect 150*e* of the working channel 150 is defined by proximal portions of the clipping members 134. When the clipping mechanism 120 is in the closed state, as shown in FIGS. 3-4, the fifth aspect 150*e* is defined between the inward-facing surfaces of the clipping members 134. Similar to the radial extensions 150*a*, 150*b*, the inward facing surfaces of the fifth aspect 150*e* can be curved (chamfered) to facilitate guiding the strip into the fifth aspect 150*e* after passing through the gap 152, which is open and does not constrain the strip. A sixth aspect of the working channel is defined as a slot 150*f* in the first clipping member 134*a* and a seventh aspect of the working channel is defined as a slot 150*g* in the second clipping member 134*b*. When the clipping mechanism 120 is in the open state, as shown in FIGS. 1-2, a gap is defined between the clipping members 134 through which the adhesive material can be passed.

It is preferable to pass the adhesive strip through the device 100 while the clipping mechanism 120 is in the closed state so that the strip can be guided through the slots 150*f*, 150*g* (e.g., sixth and seventh aspects of the working channel 150) formed in the clipping members 134. This can help keep the adhesive strip longitudinally aligned with the clipping members 134 to ensure the proper portion of the adhesive strip is cut when the clipping members 134 are closed. However, this is not required.

It should be understood that the device 100 described in FIGS. 1-8 is only exemplary and various modifications can be made without departing from the scope of the present disclosure.

In one alternative embodiment, the clipping mechanism comprises a first clipping member having a sharp clipping end and a second clipping member comprising a flat surface on its end that acts as an anvil against which the adhesive strip can be severed. In this embodiment, the sharp clipping end of the first clipping member is pressed against the flat end of the second clipping member to sever the adhesive material. Similar to the device 100, the clipping members in this embodiment may be opened and closed via respective lever systems or by any other suitable mechanism.

In another alternative embodiment, the clipping mechanism can be arranged so that only one of the clipping members is rotatable to open and close the clipping mechanism. In this embodiment, a first clipping member is non-rotatably fixed to the body of the device so that it extends substantially longitudinally from the device in a fixed orientation. A second clipping member may then be arranged similarly to one of the clipping members described for the device 100, e.g., so that it may be rotated away from the first clipping member. The adhesive strip can then be passed distally through the clipping members so that one edge of the adhesive strip rests against the first (stationary) clipping member, providing a first surface against which the second clipping member can be pressed when the second clipping member is rotated toward the first clipping member to close the clipping mechanism and cut the adhesive strip. It should be understood that, in this embodiment, the lever system can be designed for rotating only the second clipping member and can be simplified relative to the clipping mechanism described for the device 100.

In still another alternative embodiment, the adhesive material comprises a cylindrical wire of any desired diameter. In this embodiment, the working channel extending through the entire device may then have a circular cross section with a cross-sectional area selected to permit the wire to slide freely therein but which has an inner diameter close enough to the outer diameter of the wire to prevent buckling of the wire.

Figure 9:
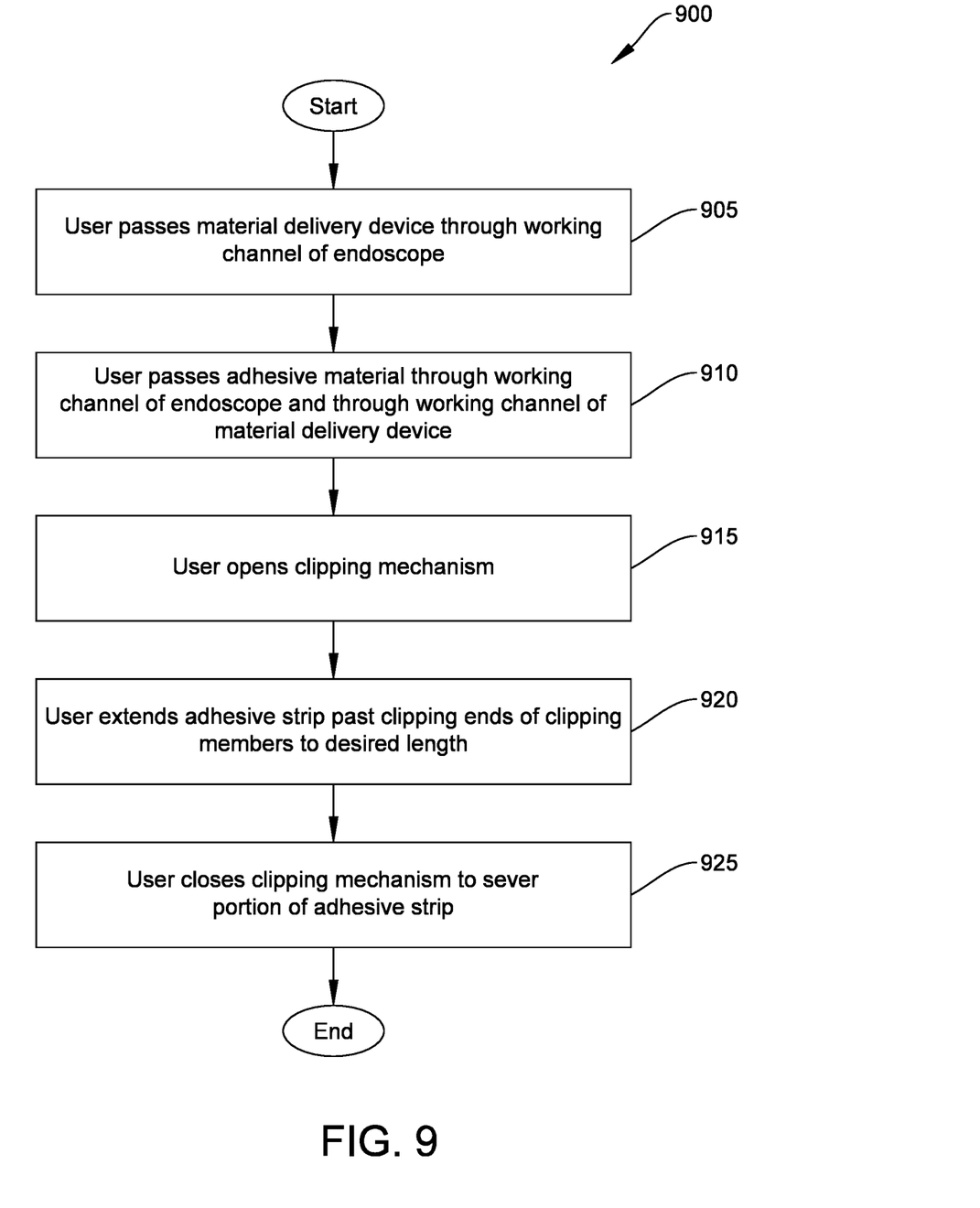
FIG. 9 shows a method for deploying and manipulating the application of an adhesive material in an endoscopic procedure according to various exemplary embodiments.

FIG. 9 shows a method 900 for deploying and manipulating the application of an adhesive material in an endoscopic procedure according to various exemplary embodiments. The method 900 is described with respect to the 100 of FIGS. 1-8. However, as described above, alternative embodiments of the device may be used in a substantially similar manner.

In 905, a user, e.g., an operating physician, passes the device 100 through the working channel of an endoscope. At this point, the endoscope can be already positioned adjacent to a target site in a living body or it may be advanced to the target site after the device 100 has been fed through the working channel to a position adjacent to a distal end of the endoscope. In particular, the target site may be a bleed site in the GI tract. The device 100 is passed through the endoscope with the clipping mechanism 120 in the closed state and extended, in the closed state, out of the distal end of the endoscope until it is adjacent to the bleed site. The user then ensures, using the vision system of the endoscope, that the device 100 is positioned as desired (e.g., so that the clipping mechanism 120 can be opened without contacting any tissue in or around the bleed site).

In 910, the user passes the adhesive material through the working channel 150 of the device 100. The adhesive material may comprise, for example, a mucoadhesive material such as chitosan formed into a long, thin strip. As described above, the adhesive strip may be formed of any desired length and can optionally be attached at a proximal end to a push/pull wire or plunger that can be controlled by the user. Furthermore, as indicated above, if desired, this may be done before the device 100 is inserted into the endoscope and the device 100 may even be pre-loaded with adhesive material when received by the user.

In this example, the adhesive strip is passed through the device 100 while the clipping mechanism 120 is in the closed state. In the closed state, the adhesive strip is guided to the clipping ends 140 of the clipping members 134 through aspects of the working channel 150 including slots 150f, 150g in the clipping members 134. However, this is not required, and the adhesive strip can also be passed through the device 100 while the clipping mechanism 120 is in the open state.

In 915, the user opens the clipping mechanism 120. As described above, the clipping mechanism 120 can be opened via a push/pull wire coupled to a plunger 122 extending through a proximal portion 104 of the body 102 of the device 100. The plunger 122 is then translated distally, causing the joining member 124 to translate proximal ends of the lever members 128 distally. The clipping members 134 are rotatably coupled (and positionally fixed) to the distal ends of the longitudinal members 110 of the distal portion 106 of the body 102, causing the distal ends of the lever members 128 and the proximal ends of the clipping members 134 to translate, rotating the clipping members 134 to the open state.

In 920, the user extends the adhesive strip distally past the clipping ends 140 of the clipping members 134 to a desired length. The adhesive strip can be applied to the target site.

In 925, the user closes the clipping mechanism 120 so that the portion of the strip extending past the clipping ends 140 is severed and remains in place at the target site.

Steps 915-925 can be repeated as desired. If the adhesive material is exhausted or nearly exhausted, prior to a sufficient number of strip portions being applied to the target site to the satisfaction of the user, the remaining portion of strip can be removed proximally from the endoscope and a second strip can be passed down the endoscope, as described in 910.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A device for applying an adhesive material to a target site in an endoscopic procedure, comprising:
   a body sized and shaped to be passed through an endoscope working channel of an endoscope; and
   a clipping mechanism comprising first and second clipping members, at least the first clipping member being rotatably coupled to a distal end of the body so that the clipping mechanism can be transitioned between a closed state, in which distal ends of the clipping members are in abutting contact, and an open state, in which the first clipping member is rotated away from the second clipping member to allow the adhesive material to be extended distally past the distal ends of the clipping members,
   wherein a device working channel of the device is formed in the body and components of the clipping mechanism, the device working channel extending longitudinally through an entirety of the device so that the adhesive material can be passed into a proximal end of the device working channel, through the device working channel, and distally past the distal ends of the clipping members when the clipping mechanism is in the open state, whereupon the clipping mechanism can be transitioned into the closed state and a portion of the adhesive material can be severed and applied to the target site.

2. The device of claim 1, wherein the adhesive material is formed into a strip and the device working channel comprises an oval or rectangular cross section for guiding the strip through the device.

3. The device of claim 2, wherein the body comprises a proximal portion including a channel and the clipping mechanism includes a plunger, the channel being sized and shaped to receive the plunger, wherein the device working channel extends through the plunger.

4. The device of claim 3, wherein the clipping mechanism includes a joining member coupled to or formed with the plunger, wherein a proximal end of at least a first lever member is rotatably coupled to the joining member and a proximal end of the first clipping member is rotatably coupled to a distal end of the first lever member, wherein the device working channel extends through the joining member.

5. The device of claim 4, wherein, in the closed state, the plunger is in a proximal position in the channel, the proximal end of the first lever member is in a proximal position, and the first clipping member extends distally.

6. The device of claim 5, wherein, in the open state, the plunger is in a distal position in the channel, the proximal end of the first lever member is in a distal position, and the first lever member and the first clipping member are rotated so that the distal end of the first clipping member is rotated away from the second clipping member.

7. The device of claim 2, wherein the adhesive material is formed as a wire and the device working channel comprises a circular cross-section for guiding the strip through the device.

8. The device of claim 1, wherein the distal end of at least the first clipping member comprises a sharp edge for severing the adhesive material.

9. The device of claim 1, wherein the device working channel comprises a slot formed in at least the first clipping member.

10. The device of claim 1, wherein the second clipping member is rotatably coupled to the distal end of the body and, when the device is transitioned into the open state, the second clipping member is rotated away from the first clipping member.

11. The device of claim 10, wherein the first clipping member is biased to rotate in a first direction and the second clipping member is biased to rotate in a second direction opposite the first direction when the clipping mechanism is actuated via longitudinal translation of a plunger of the clipping mechanism.

12. The device of claim 1, wherein the first clipping member is rotatably coupled to distal end of the body via a pin extending through pin holes in the first clipping member and the distal end of the body.

13. The device of claim 1, wherein the second clipping member is fixed or formed integrally with the distal end of the body and the first clipping member and only the first clipping member is rotatable to open or close the clipping mechanism.

14. The device of claim 1, wherein the clipping mechanism is actuated by a pull wire coupled to a proximal end of the clipping mechanism.

15. The device of claim 1, wherein the adhesive material is chitosan.

16. A method for applying an adhesive material to a target site in an endoscopic procedure, comprising:

passing a material delivery device through an endoscope working channel of an endoscope, the device comprising a body sized and shaped to be passed through the endoscope working channel and a clipping mechanism comprising first and second clipping members, at least the first clipping member being rotatably coupled to a distal end of the body so that the clipping mechanism can be transitioned between a closed state, in which distal ends of the clipping members are in abutting contact, and an open state, in which the first clipping member is rotated away from the second clipping member to allow the adhesive material to be extended distally past the distal ends of the clipping members, wherein a device working channel of the device is formed in the body and components of the clipping mechanism, the device working channel extending longitudinally through an entirety of the device;

passing the adhesive material through the endoscope working channel into a proximal end of the device working channel, through the device working channel, and distally past the distal ends of the clipping members when the clipping mechanism is in the open state; and transitioning the clipping mechanism into the closed state to sever a portion of the adhesive material and apply the portion of the adhesive material to the target site.

17. The method of claim 16, wherein the adhesive material is formed into a strip and the device working channel comprises an oval or rectangular cross section for guiding the strip through the device.

18. The method of claim 17, wherein the adhesive material is formed into a wire and the device working channel comprises a circular cross section for guiding the strip through the device.

19. The method of claim 16, wherein the clipping mechanism is actuated by a pull wire coupled to a proximal end of the clipping mechanism.

20. The method of claim 16, further comprising:

after applying the portion of the adhesive material to the target site, transitioning the clipping mechanism into the open state;

passing a remaining portion of the adhesive material distally past the distal ends of the clipping members; and transitioning the clipping mechanism into the closed state to sever a further portion of the adhesive material and apply the further portion of the adhesive material to the target site.

* * * * *